United States Patent [19]

Guttmann et al.

[11] Patent Number: 4,788,317

[45] Date of Patent: Nov. 29, 1988

[54] AMMOXIDATION OF PARAFFINS AND CATALYSTS THEREFOR

[75] Inventors: Andrew T. Guttmann, Maple Heights; Robert K. Grasselli, Aurora; James F. Brazdil, Jr., Mayfield Village, all of Ohio

[73] Assignee: Standard Oil Company, Cleveland, Ohio

[21] Appl. No.: 47,949

[22] Filed: May 8, 1987

Related U.S. Application Data

[60] Continuation-in-part of Ser. No. 826,695, Feb. 6, 1986, abandoned, which is a division of Ser. No. 724,226, Apr. 17, 1985, Pat. No. 4,746,641, which is a continuation-in-part of Ser. No. 643,208, Aug. 22, 1984, abandoned, and a continuation-in-part of Ser. No. 919,105, Oct. 15, 1986, abandoned.

[51] Int. Cl.$^4$ ............................................. C07C 120/14
[52] U.S. Cl. ........................................ 558/319; 423/376
[58] Field of Search ............................................ 558/319

[56] References Cited

U.S. PATENT DOCUMENTS

| | | | |
|---|---|---|---|
| 3,433,823 | 3/1969 | McMahon | 558/319 X |
| 3,591,620 | 7/1971 | Yoshino et al. | 558/325 |
| 3,686,267 | 8/1972 | Taylor | 558/319 |
| 3,816,506 | 6/1974 | Taylor | 558/319 |
| 3,860,534 | 1/1975 | Harris et al. | 558/319 X |
| 3,988,359 | 10/1976 | Saito et al. | 502/202 |
| 4,010,188 | 3/1977 | Grasselli et al. | 558/319 |
| 4,039,558 | 6/1977 | Grasselli et al. | 502/206 |
| 4,049,575 | 9/1977 | Sasaki et al. | 502/202 |
| 4,051,179 | 9/1977 | Sonobe et al. | 502/211 X |
| 4,065,468 | 12/1977 | Grasselli et al. | 549/258 |
| 4,316,855 | 2/1982 | Grasselli et al. | 558/319 X |
| 4,339,394 | 7/1982 | Grasselli et al. | 558/319 X |
| 4,339,598 | 7/1982 | Guttmann et al. | 560/210 |
| 4,413,155 | 11/1983 | Suresh et al. | 558/325 X |
| 4,436,671 | 3/1987 | Furuoya et al. | 558/319 |

FOREIGN PATENT DOCUMENTS 1336136 11/1973 United Kingdom ............... 558/319

*Primary Examiner*—Joseph Paul Brust
*Attorney, Agent, or Firm*—C. S. Lynch; D. J. Untener; L. W. Evans

[57] ABSTRACT

Disclosed is a process for ammoxidation of paraffins containing 3-5 C atoms using a complex metal oxide catalyst which is essentially free of bismuth, and has the elements and the proportions which are represented by the following empirical formula:

$$VSb_mP_nA_aD_bC_cO_x$$

where
A is one of more of W, Sn, B, Mo and As;
D is one or more of Fe, Co, Ni, Cr, Mn, Cu, Pb, Zn, Se, Te and As;
C is one or more of an alkali metal, Ca, Sr, Ba, Tl and where m is greater than 1 and up to 20; n is 0-10; a is 0.2-10; b is 0-5; c is 0-1; a is equal to or less than m; b is equal to or less than m; wherein x is determined by oxidation state of the other elements present, and wherein the antimony has an average valency higher than +3 and the vanadium has an average valency lower than +5, wherein A includes at least 0.2 atoms of W, crystalline $Sb_2O_4$ is present in said catalyst, and wherein the foregoing catalyst is on a specified inorganic oxide support material.

23 Claims, No Drawings

AMMOXIDATION OF PARAFFINS AND CATALYSTS THEREFOR

This application is a continuation-in-part of application Ser. No. 826,695, filed Feb. 6, 1986, now abandoned which in turn is a division of Ser. No. 724,226, filed Apr. 17, 1985, now U.S. Pat. No. 4,746,641, issued 5-24-88, which is a continuation-in-part of parent application Ser. No. 643,208 filed Aug. 22, 1984, now abandoned. This application is also a continuation-in-part of application Ser. No. 919,105, filed Oct. 15, 1986 now abandoned.

This invention relates to the catalytic ammoxidation of paraffins containing from 3 to 5 carbon atoms to $\alpha,\beta$ unsaturated nitriles, especially paraffins containing 3 to 4 carbon atoms. Most important is the ammoxidation of propane to acrylonitrile and the ammoxidation of isobutane to methacrylonitrile.

Because of the price differential between propylene and propane an economic incentive exists for the development of a viable catalytic process for conversion of propane to acrylonitrile.

Earlier attempts to develop an efficient process for the ammoxidation of propane to acrylonitrile produced either insufficient yields or processes that necessitated adding halogen promoters to the feed. The latter procedure would require not only reactors made of special corrosion resistant materials, but also the quantitative recovery of the promoter. The added costs thus eliminated the advantage of the propane/propylene price differential.

It is thus an object of the present invention to provide an improved process for the ammoxidation of paraffins to unsaturated nitriles.

It is a further object of the invention to provide new catalysts for such reaction.

It is still another object of the present invention to provide improved methods of preparing such catalysts, and precursors for such catalysts.

Still another object is to provide an improved catalytic ammoxidation process for making unsaturated nitriles from lower paraffins without the use of halogen promoters.

Other objects, as well as aspects, features and advantages, of the present invention will become apparent from a study of the accompanying disclosure and the claims.

These and other objects are achieved by the present invention according to one aspect of which there is provided a process for the ammoxidation of paraffins containing 2 to 5 carbon atoms by the catalytic reaction of such paraffins with oxygen and ammonia by catalytic contact with an essentially bismuth free complex metal oxide catalyst having the ingredients and the proportions which are represented by the following empirical formula:

$$VSb_mA_aD_bC_cO_x, \qquad \text{formula (1)}$$

where
A is one or more of W, Sn, Mo, B and Ge;
D is one or more of Fe, Co, Ni, Cr, Mn, Cu, Zn, Se, Te, Pb and As;
C is one or more of an alkali metal, Ca, Sr, Ba, and Tl
and where m is greater than 1 and up to 20 (usually 2-10, most usually 3-7); a is 0-10; b is 0-5; c is 0-1; a is equal to or less than m; b is equal to or less than m; wherein x is determined by the oxidation state of the other elements, and wherein the antimony has an average valency higher than +3 and the vanadium has an average valency lower than +5, wherein crystalline $Sb_2O_4$ is present in said catalyst, and wherein the foregoing catalyst is on a inorganic oxide support material. All of the subscripts in formula (1) are of course atoms. A now preferred support material is alumina or silica-alumina, as further discussed herein.

The catalysts of formula (1) can, in general, contain oxides of other elements not set forth in formula (1), as long as they do not materially detrimentally affect the catalytic ammoxidation of the paraffin to the desired nitriles. When bismuth is optionally present in oxidized form as part of the catalyst of formula (1), it is usually present in amounts of no more than 0.2 atoms of Bi per atoms of V.

In the catayst of the invention having the ingredients and proportions which are represented by formula (1), in an especially advantageous embodiment, P is also present in the catalyst inan amount up to 10 atoms P per atom of V (usually 0.1-5 atoms, most usually 0.1-1 atoms per atom of V). Thus, the formula (1) in such event could be written as $$VSb_mP_nA_aD_bC_cO_x$$

where a, b, c, A, D and C are as before and n is greater than zero and up to 10 (usually 0.1-5, most usually 0.1-1).

Such P-containing catalysts are particularly useful when the catalysts contain tungsten and have an alumina-containing support/diluent as disclosed herein.

It should be noted that the present ammoxidation reaction is effected in the substantial absence of halogen or sulfur or compounds thereof. Preferably also, a halide or halogen is not employed in the preparation of the catalyst precursor of the invention.

The present process is especially useful in the ammoxidation of propane and isobutane.

Especially useful catalyst compositions of the foregoing description are those in which a is at least 1 and includes at least 1 atom of W.

According to the present invention, the foregoing catalysts are prepared under conditions such that in the final composition the average oxidation state of vanadium is less than +5, and often approaches +3. One method of the present invention for preparing the catalysts is by a redox reaction between a compound of trivalent antimony such as $Sb_2O_3$ and a compound of pentavalent vanadium, such as $V_2O_5$, during which at least part of the antimony is oxidized and at least part of the the vanadium reduced, presumably according to the equation $$Sb_2O_3 + V_2O_5 \rightarrow 2VSbO_4 \qquad \text{Equation (1)}$$

The foregoing redox reaction was described by Birchall and Sleight (*Inorganic Chem.* 15, 868–70 [1976]) and by Berry et al. (*J. Chem. Soc. Dalton Trans.*, 1983, 9–12), who effected the reaction by heating a dry mixture of the above reactants at temperatures above 600° C.

We have now found that a redox reaction can successfully and more conveniently be carried out in an aqueous medium by heating at a temperature of at least 80° C. and up to 200° C., for instance, by heating an aqueous dispersion of a $V^{5+}$ compound, such as NH$_4$VO$_3$ or V$_2$O$_5$, with an Sb$^{3+}$ compound in excess over that called for by Equation (1), such as by reacting Sb$_2$O$_3$ and NH$_4$VO$_3$ (or V$_2$O$_5$). This step is followed by evaporation, drying and then calcining the product in an oxygen-containing atmosphere, such as air, at from 350° to 700° or 750° C., usually 400° to 600° C. The length of the calcination period may range from 30 minutes to 12 hours, but satisfactory catalysts are usually obtained by calcination at such temperatures for a period of from 1 to 5 hours.

At least part of the excess of trivalent antimony compound, such as Sb$_2$O$_3$, is oxidized to Sb$_2$O$_4$ during the calcination in molecular oxygen containing atmosphere, such as air. The presence in the finished catalyst of the excess antimony oxide as Sb$_2$O$_4$ results in superior catalytic performance.

The ingredients of the catalysts other than vanadium and antimony (and of course part of the oxygen) can be incorporated after completion of the foregoing redox reaction. Thus, the additives P, A, D and C can be added in the slurry after the redox reaction, or the solid particles containing the vanadium and antimony values after separation from the aqueous medium can be coated or impregnated in a known manner with such additives at any suitable stage prior to final calcination of the catalyst, by methods generally known in the art, using oxides, hydroxides, acids, salts (particularly organic salts such as acetates), and other compounds of such elements.

According to one aspect of the present process there is provided a catalyst precursor which comprises an aqueous slurry of the redox reaction product of a V$^{5+}$ compound and an Sb$^{3+}$ compound where the Sb$^{3+}$ compound is in excess, said redox reaction product having the empirical formula

VSb$_m$O$_x$, formula (2)

in admixture with a solid, particulate inorganic oxide support material, where m is >1 and up to 20 and wherein the unreacted antimony is in the form of antimony trioxide, the V has an average valence less than +5 and the reacted Sb has an average valence more than +3, and wherein the atoms of Sb over m=1 are present at least in part as Sb$_2$O$_3$ and the support material is from 10 to 90 weight percent, usually from 20-75 weight percent, of the total slurry solids on a dry oxide basis.

Usually, in the above precursor slurries m is 2-10, more usually 3-7.

The catalyst precursor slurry can be dried and calcined in a molecular oxygen containing gas at temperatures of 350° to 850° C., more often, 350° to 700° C., usually 400° to 600° C. or 650° C., to produce a catalyst useful in the process of the invention for ammoxidizing C$_3$ to C$_5$ paraffins. The additives A, D and/or C, if any, can be added in the slurry after the redox reaction, or the solid particles containing the vanadium and antimony values after separation from the aqueous medium can be coated or impregnated in a known manner with such additives at any suitable stage prior to final calcination of the catalyst.

It should be noted that when the oxidation of the unreacted excess Sb$_2$O$_3$ during calcination is prevented by an exclusion of oxygen, such as by calcination in a nitrogen atmosphere, a very inferior catalyst results.

If vanadium-antimony catalysts are prepared by using pentavalent vanadium and pentavalent antimony compounds, thus eliminating the redox reaction, both the vanadium and antimony remain in the high oxidation state and the resulting catalyst is very inferior, with or without additives. It has also been found that inferior catalysts are made when the vanadium-antimony compound is made by reacting Sb$_2$O$_3$ and V$_2$O$_5$ (or other V$^{5+}$ compound) in the presence of compounds that may act as oxidizing or reducing agents, such as nitric acid, nitrates, or multivalent ions, since these tend to interfere with the desired redox reaction between antimony and vanadium.

Thus, according to the present invention the superior catalytic performance in paraffin ammoxidation is obtained with the catalysts of the invention which contain a complex vanadium-antimony oxide composition with vanadium in a low oxidation state and antimony in a high oxidation state greater than +3, plus some excess antimony oxide as crystalline Sb$_2$O$_4$, plus an inorganic oxide support, as will be shown by comparative examples hereafter.

Whether or not tungsten is present in the catalysts shown in formula (1) of the catalysts of the invention, the promoting element Sn from the A Group and the promoting elements Te and Fe from the D Group give especially good results in the catalyst of the invention, either when one or any two or three of these elements are present.

Thus, an especially useful group of complex metal oxide catalysts of the invention for use in the paraffin ammoxidation process of the invention are the essentially bismuth free catalysts having the elements and the proportions which are represented by the formula

VSb$_m$A$_a$D$_b$O$_x$ formula (3)

where

A is one or more of W and Sn;

D is one or more of Fe and Te; and where m is greater than 1 and up to 20 (usually 2-10, most usually 3-7); a is 0-10; b is 0-5; a is equal to to less than m; b is equal to or less than m and usually is at least 0.2; wherein x is determined by the oxidation state of the other elements; and wherein the antimony has an average valency higher than +3 and the vanadium has an average valency lower than +5, wherein crystalline Sb$_2$O$_4$ is present in said catalyst, and wherein the foregoing catalyst is on a inorganic oxide support material. Now preferred support materials are silica-alumina and alumina as previously discussed herein.

In formulas (1) and (3) subscript a usually is at least 0.2, more usually at least 0.4 to 0.5. In formula (1) at least 0.2 atoms of W are preferably present (more often at least 0.4 atoms) per atom of V, and the total of W plus Sn atoms (if any Sn is present) is usually at least 0.4 atoms. The same is true of formula (3).

Especially useful catalyst compositions of the foregoing description are those in which a is at least 1 and includes at least 1 atom of W.

The catalysts of the present invention are essentially free of uranium. Moreover, in the process of the invention, essentially no sulfur or sulfur compounds, or halogen or halogen compounds, are present in the reaction mixture.

Phosphorus, tungsten and the optional elements shown in formulas (1) and (3) can be incorporated in the base vanadium/antimony/support precursor slurry or are added to the solids recovered from the slurry by methods generally known in the art, using oxides, hydroxides, acids, salts (particularly organic salts such as acetates), and other compounds of such elements. Examples of such incorporation are shown in the specific examples hereinafter.

Tungsten is advantageously incorporated as ammonium meta- or orthotungstate, tungstic acid, or tungsten trioxide. P can be introduced, for instance, as ammonium phosphate or $(NH_4)_2HPO_4$ or phosphoric acid.

The catalyst support not only improves mechanical stability of the catalysts, but the catalytic activity is significantly improved, especially in the case of alumina and silica-alumina. This is amply shown in the examples. Besides alumina and silica-alumina other supports that can be used are silica, titania, silica-titania, $Nb_2O_5$, silica-niobia, silica-zirconia, zirconia, and magnesia, etc.

In the usual practice of the invention the catalyst support/diluent of the empirical formula of the catalyst of the invention is not an oxide of an element named in such empirical formula.

Now preferred support materials for not only improving mechanical stability but also for improving the yield of the desired nitriles are selected from silica-alumina and alumina having 20-100, usually 50-100, preferably 60-100 weight percent alumina; silica-titania and titania having 20-100 wieght percent titania; silica-zirconia and zirconia having 80-100 weight percent zirconia; and silica-niobia and niobia having 30-100 weight percent niobia ($Nb_2O_5$).

The weight ratio of the catalyst having the ingredients of empirical formulas (1) or (3) to the support material can vary from 9:1 to 1:9.

In the ammoxidation of the present invention, the reaction is preferably carried out in the gas phase by contacting a mixture of the paraffin, ammonia and a molecular oxygen containing gas, such as air, with a catalyst of the invention contained in a fixed bed, a gravity flowing bed, a fluidized bed or a fast transport reactor mode. It also possible to include additional diluents such as steam, nitrogen, carbon dioxide or helium.

The mole ratio of oxygen to the paraffin, such as propane, can vary from 0.1:1 to 10:1, more often 0.5:1 to 4:1, and a ratio in the range from 1:1 to 3:1 is usual. The ammonia to paraffin (such as propane) ratio can vary from 0.06:1 to 5:1, more often 0.5:1 to 5:1, but is usually from 1:1 to 5:1. When ammonia to paraffin ratios are much less than 1, various undesirable oxygenated derivatives of the paraffin can be formed.

The reaction temperature can vary from 400° to 650° C., but is usually 460° to 520° C. The latter temperature ranges are especially useful in the case of propane ammoxidation to acrylonitrile.

The average contact time can be from 0.02, usually 1, up to 20 seconds, but is usually from 0.2 to 10 seconds, more often 2 to 8 seconds. However, higher or lower contact times are within the scope of the process of the invention.

The catalysts of the present invention are believed to be unique. U.S. Pat. No. 3,860,534; 1975, describes catalysts that contain only vanadium and antimony but these require water washing after preparation and then redrying by a laborious and time consuming procedure.

The following examples of the invention are exemplary and should not be taken as in any way limiting.

In the examples the conversion, yield and selectivity are defined as follows:

$$\text{conversion} = \frac{\text{moles paraffin reacted}}{\text{moles paraffin charged}} \times 100\ (\%)$$

$$\text{yield} = \frac{\text{moles product produced}}{\text{moles paraffin charged}} \times 100\ (\%)$$

$$\text{selectivity} = \frac{\text{moles product produced}}{\text{moles paraffin reacted}} \times 100\ (\%)$$

The term per pass conversion when used herein has the same definition as yield.

EXAMPLE 1

A catalyst having the composition 50% $VSbO_x + 50\%\ SiO_2$ was prepared as followed. In a flask equipped for heating under reflux with agitation there was placed 100 g. of 40 percent silica sol with 30 ml additional water, and 24.6 g. $Sb_2O_3$. To this mixture there was added a hot solution of 19.8 g. $NH_4VO_3$, and the slurry was stirred and boiled under reflux for 12-16 hours to effect the redox reaction between vanadium and antimony. It was then transferred to an open beaker and heated with stirring on a hot plate to remove the bulk of the water. The resulting wet product was dried in air overnight at 110°-120° C., then further heated at 350° C. for 5 hours, screened to the desired particle size and calcined in air at 530° C. for 3 hours.

EXAMPLE 2

A catalyst having the composition 50% $VSbWO_x + 50\%\ SiO_2$ was prepared similarly to that of Example 1 from 100 g. 40% silica sol, 12.4 g. $Sb_2O_3$, and 10.0 g. $NH_4VO_3$, but after the redox reaction, 23.0 g. ammonium metatungstate in 50 ml $H_2O$ was added to the mixture. The evaporation, drying and calcination were then conducted in the same manner as in Example 1.

EXAMPLES 3-14

Additional catalysts, listed in Table I, were prepared according to examples 1 and 2, but with varying ratios of V, Sb, and W. Catalysts supported on silica-alumina were made by substituting hydrated alumina (85% as $Al_2O_3$) for part of the 40 percent silica sol, the total amount of support remaining at 50 wt. percent. In some catalysts, $V_2O_5$ was used as vanadium source instead of $NH_4VO_3$. The catalysts were tested for performance in propane ammoxidatio using a fixed bed 5 cc. microreactor with a preheat leg immersed in a temperature-controlled molten salt bath. The reaction feed (propane, ammonia, air) was metered through mass flow controllers into a mixing column, then introduced into the bottom of the reactor through the preheat leg. As an additional diluent (optional) water was fed through a septum at the top of the preheat leg, using a syringe pump. The catalyst charge was 5 cc of 20-35 mesh particles in a fixed bed reactor. The reaction temperature was 500° C., and the total feed flow was such as to obtain an average contact time of 4.5 seconds. The feed ratios are listed with the results in the following Tables. The effluent from the reactor was recovered and analyzed, and the amounts of acrylonitrile, by-products and unreacted feed determined. The results for catalysts of Examples 1-14 are listed in Table I. Since HCN is a valuable co-product of acrylonitrile production, its yields and selectivities are included.

The above examples show that vanadium antimonates exhibit significant catalystic activity in the production of acrylonitrile by ammoxidation of propane. They also show the significant effects of the excess antimony, the catalyst support, and the presence of tungsten on the catalytic performance, and the performance variations with reaction conditions (e.g. $O_2/C_3$ ratio). Examples No. 9 and 10 illustrate different sources of vanadium that can be used. As comparative examples, Examples No. 4 and 7 show the importance of the oxidation of the excess antimony oxide present in the catalyst to an oxidation state greater than +3. Note that all catalysts of the invention herein contained crystalline $Sb_2O_4$, while examples 4 and 7 did not.

EXAMPLES 15–25

To show the effect of addition of one or more additional elements to the catalysts of this invention, catalysts listed in Table II were prepared according to procedures of Examples No. 1 and 2. The additional elements were incorporated after the completion of the redox reaction of $Sb_2O_3$ with $NH_4VO_3$ or $V_2O_5$. By way of illustration, tellurium was added as $TeO_2$, tin as aqueous 18 percent $SnO_2$ sol, and iron as ferrous acetate. The catalysts were supported on silica-alumina (as in Examples 5–14), except for Example 23 where silica-titania was used. The catalysts were tested as already described, the results are shown in Table II.

EXAMPLES 26–29

To show the importance of forming a vanadium antimonate via a redox reaction between trivalent antimony and pentavalent vanadium, a catalyst having the empirical formula of the catalyst of Example 19 ($VSb_5W_{0.5}Fe_{0.5}Te_{0.5}O_x$) was prepared as follows.

To a warm slurry of 37.6 Catapal SB hydrated alumina, AlO(OH), and 20.0 g. 40% silica sol in water, there was added a hot solution of 4.12 g. $NH_4VO_3$ in 100 ml $H_2O$, followed by 237.5 g. of aqueous 12% $Sb_2O_5$ sol (containing 28.5 g. $Sb_2O_5$). To this mixture there was added 4.75 g. ammonium metatungstate in 10 ml $H_2O$, 2.81 g. $TeO_2$, and 7.12 g. $Fe(NO_3)_2 9H_2O$ in 15 ml $H_2O$. The mixture was boiled down, with agitation, to a paste, dried overnight at 115°–20° C., treated 5 hours at 350° C., screened and calcined for 3 hours at 530° C.

In the same manner, but without the additional elements, a catalyst having the empirical formula of the catalyst of Example 6 ($VSb_5O_x$) was also made. Both catalysts were tested in the described manner; the results are shown in Table III.

In the above comparative examples 26 to 29 the catalysts were prepared in such a manner that a redox reaction between antimony and vanadium to form a vanadium antimonate could not take place, and both elements remained in a high oxidation state. A comparison of the results of Table III with the corresponding results of Examples 6, 8, 19 and 20 show clearly that the catalysts of this invention are greatly suprior to those of Table III, producing much higher product yields and selectivities. At conditions of increased oxygen/propane ratio where the performance of the catalysts of this invention is further improved, the catalyst of the comparative examples 28 and 29 becomes even worse.

The excellent results shown by the examples of the invention that are in Tables I, II and III are, furthermore, achieved by using surprisingly low calcination temperatures in catalyst preparation, in contrast to other vanadium-antimony compositions described in the prior art.

EXAMPLES 30–41

To show the specific effect of the support on catalyst performance, in addition to its normal function to give physical strength and attrition resistance, the runs shown in Table IV were carried out.

TABLE I

| | | | Ammoxidation of Propane | | | | | | |
|---|---|---|---|---|---|---|---|---|---|
| Example No. | Catalyst[1] | Support[1] | Source | Calcination | $O_2/C_3$ | % Conv $C_3$ | % select. AN | % select. HCN | % yield AN | % yield HCN |
| 1 | $VSbO_x$ | $SiO_2$ | $NH_4VO_3$ | AIR | 1.5 | 15.4 | 23.3 | 13.6 | 3.6 | 2.1 |
| 3 | $VSb_5O_x$ | $SiO_2$ | $NH_4VO_3$ | AIR | 1.5 | 21.6 | 43.5 | 16.0 | 11.6 | 4.3 |
| 4 | $VSb_5O_x$ | $SiO_2$ | $NH_4VO_3$ | $N_2$ | 1.5 | 3.4 | 32.9 | 22.5 | 1.1 | 0.8 |
| 2 | $VSbWO_x$ | $SiO_2$ | $NH_4VO_3$ | AIR | 1.5 | 14.7 | 29.8 | 14.7 | 4.4 | 2.2 |
| 5 | $VSbO_x$ | SIAL | $NH_4VO_3$ | AIR | 1.5 | 39.3 | 44.3 | 5.4 | 17.4 | 2.1 |
| 6 | $VSb_5O_x$ | SIAL | $NH_4VO_3$ | AIR | 1.5 | 47.6 | 44.4 | 1.4 | 20.5 | 0.7 |
| 7 | $VSb_5O_x$ | SIAL | $NH_4VO_3$ | $N_2$ | 1.5 | 27.6 | 19.1 | 5.7 | 5.3 | 1.6 |
| 8 | $VSb_5O_x$ | SIAL | $NH_4VO_3$ | AIR | 2.0 | 63.6 | 46.8 | 7.2 | 29.6 | 4.6 |
| 9 | $VSb_5O_x$ | SIAL | $V_2O_5$ | AIR | 1.5 | 43.9 | 47.7 | 1.4 | 20.9 | 0.6 |
| 10 | $VSb_5O_x$ | SIAL | $V_2O_5$ | AIR | 2.0 | 64.0 | 45.6 | 2.2 | 29.2 | 1.4 |
| 11 | $VSbWO_x$ | SIAL | $NH_4VO_3$ | AIR | 1.5 | 32.8 | 29.8 | 2.2 | 9.8 | 0.7 |
| 12 | $VSb_5W_{0.5}O_x$ | SIAL | $NH_4VO_3$ | AIR | 1.5 | 50.0 | 51.2 | 3.7 | 25.6 | 1.9 |
| 13 | $VSb_5WO_x$ | SIAL | $NH_4VO_3$ | AIR | 1.5 | 46.9 | 53.3 | 4.4 | 25.0 | 2.1 |
| 14 | $VSb_5WO_x$ | SIAL | $NH_4VO_3$ | AIR | 2.0 | 73.3 | 52.4 | 7.8 | 38.4 | 5.7 |

[1]SIAL = silica-alumina having 20% $SiO_2$ and 80% $Al_2O_3$
Temp.: 500° C.
Contact time: 4.5 sec
Feed ratio: $C_3/NH_3/O_2/N_2/H_2O$ = 1/2 /1.5(2.0)/5.7(7.5)/3
50 wt. % catalyst support
Calcination @ 530° C. in air or $N_2$

TABLE II

| | | Ammoxidation of Propane | | | | | |
|---|---|---|---|---|---|---|---|
| Example No. | Catalyst[1] | Source | $O_2/C_3$ | % Conv. $C_3$ | % select. AN | % select. HCN | % yield AN | % yield HCN |
| 15 | $VSb_5TeO_x$ | $NH_4VO_3$ | 1.5 | 44.1 | 44.1 | 0.3 | 20.4 | 0.1 |
| 16 | $VSb_5SnO_x$ | $NH_4VO_3$ | 1.5 | 29.3 | 41.0 | 1.5 | 16.1 | 0.6 |
| 17 | $VSb_5Te_{0.5}Sn_{0.5}O_x$ | $NH_4VO_3$ | 1.5 | 41.0 | 53.2 | 3.4 | 21.8 | 1.4 |
| 18 | $VSb_5W_{0.5}Fe_{0.5}O_x$ | $NH_4VO_3$ | 1.5 | 46.5 | 45.7 | 6.5 | 21.3 | 3.0 |
| 19 | $VSb_5W_{0.5}Fe_{0.5}Te_{0.5}O_x$ | $NH_4VO_3$ | 1.5 | 49.7 | 53.3 | 5.5 | 26.5 | 2.7 |

TABLE II-continued

Ammoxidation of Propane

| Example No. | Catalyst[1] | Source | $O_2/C_3$ | % Conv. $C_3$ | % select. AN | % select. HCN | % yield AN | % yield HCN |
|---|---|---|---|---|---|---|---|---|
| 20 | $VSb_5W_{0.5}Fe_{0.5}Te_{0.5}O_x$ | $NH_4VO_3$ | 2.0 | 66.1 | 48.1 | 7.0 | 31.8 | 4.6 |
| 21 | $VSb_5W_{0.5}Fe_{0.5}Te_{0.5}O_x$ | $V_2O_5$ | 1.5 | 39.9 | 56.1 | 3.9 | 22.4 | 1.6 |
| 22 | $VSb_5W_{0.5}Fe_{0.5}Te_{0.5}O_x$ | $V_2O_5$ | 2.0 | 65.8 | 50.6 | 6.4 | 33.3 | 4.2 |
| 23 | $VSb_5W_{0.5}Fe_{0.5}Te_{0.5}O_x1$ | $NH_4VO_3$ | 2.0 | 42.5 | 53.3 | 1.7 | 22.7 | 0.7 |
| 24 | $VSb_5W_{0.5}Te_{0.5}Sn_{0.5}O_x$ | $NH_4VO_3$ | 1.5 | 51.1 | 59.1 | 3.6 | 30.2 | 1.8 |
| 25 | $VSb_5W_{0.5}Te_{0.5}Sn_{0.5}O_x$ | $NH_4VO_3$ | 2.0 | 68.8 | 56.7 | 5.9 | 39.0 | 4.1 |

[1]Supported on 50% silica-titania (20% $SiO_2$, 80% $TiO_2$)
Temp.: 500° C.
Contact time: 4.5 sec
Feed ratio: $C_3/NH_3/O_2/N_2/H_2O$ = 1/2 /1.5(2.0)/5.7(7.5)/3
catalyst support: 50% silica-alumina (20% $SiO_2$, 80% $Al_2O_3$)
calcination: @ 530° C. in air

TABLE III

Ammoxidation of Propane

| Example No. | Catalyst[1] | $O_2/C_3$ | % Conv. $C_3$ | % select. AN | % select. HCN | % yield AN | % yield HCN |
|---|---|---|---|---|---|---|---|
| 26 | $VSb_5O_x$ | 1.5 | 42.2 | 39.3 | 3.5 | 16.6 | 1.5 |
| 27 | $VSb_5O_x$ | 2.0 | 60.0 | 37.0 | 2.6 | 22.2 | 1.6 |
| 28 | $VSb_5W_{0.5}Fe_{0.5}Te_{0.5}O_x$ | 1.5 | 37.9 | 44.7 | 5.7 | 16.9 | 2.2 |
| 29 | $VSb_5W_{0.5}Fe_{0.5}Te_{0.5}O_x$ | 2.0 | 45.0 | 29.3 | 1.5 | 13.2 | 0.7 |

Temp.: 500° C.
Contact time: 4.5 sec
Feed ratio: $C_3/NH_3/O_2/N_2/H_2O$ = 1/2 /1.5(2.0)/5.7(7.5)/3
catalyst support: 50% silica-alumina (20% $SiO_2$, 80% $Al_2O_3$)
calcination: @ 530° C. in air

TABLE IV

AMMOXIDATION OF PROPANE

| Example No. | Catalyst | Support Composition wt. % $SiO_2$ | $Al_2O_3$ | $TiO_2$ | $ZrO_2$ | $Nb_2O_5$ | $O_2/C_3$ | % Conv. $C_3$ | % Yield AN |
|---|---|---|---|---|---|---|---|---|---|
| 30 | $VSb_5O_x$ (no support) | 0 | 0 | 0 | 0 | 0 | 1.5 | 31.8 | 10.1 |
| 31 | $VSb_5O_x$ (no support) | 0 | 0 | 0 | 0 | 0 | 2.0 | 40.0 | 11.5 |
| 32 | $VSb_5O_x$ | 100 | 0 | 0 | 0 | 0 | 1.5 | 26.6 | 11.6 |
| 33 | $VSb_5O_x$ | 20 | 80 | 0 | 0 | 0 | 1.5 | 49.3 | 24.7 |
| 34 | $VSb_5O_x$ | 20 | 80 | 0 | 0 | 0 | 2.0 | 63.3 | 29.6 |
| 35 | $VSb_5O_x$ (no support) | 0 | 0 | 0 | 0 | 0 | 2.0 | 42.9 | 11.2 |
| 36 | $VSb_5WO_x$ | 100 | 0 | 0 | 0 | 0 | 2.0 | 45.8 | 11.8 |
| 37 | $VSb_5WO_x$ | 20 | 80 | 0 | 0 | 0 | 2.0 | 66.7 | 40.0 |
| 38 | $VSb_5WO_x$ | 80 | 20 | 0 | 0 | 0 | 2.0 | 48.3 | 22.2 |
| 39 | $VSb_5WO_x$ | 80 | 0 | 20 | 0 | 0 | 2.0 | 42.4 | 19.9 |
| 40 | $VSb_5WO_x$ | 15 | 0 | 0 | 85 | 0 | 2.0 | 31.1 | 17.0 |
| 41 | $VSb_5WO_x$ | 46 | 0 | 0 | 0 | 54 | 2.0 | 44.3 | 18.9 |

Conditions:
$C_3/NH_3/O_2/N_2/H_2O$ = 1/2/1.5(2)/5.7(7.5)/3
Temperature 500° C.
Contact Time 4.5 Sec.
(1) In all supported catalysts in Tables I-IV the support was 50 weight percent of the total catalyst composition

EXAMPLE 42

In this example the catalyst was $VSb_5WO_x$ supported on an equal weight of alumina. The catalyst charge was 5 cc of 20-35 mesh particles in the fixed bed reactor.

The feed ratios were

Propane/$NH_3$/$O_2$/$N_2$/$H_2O$ = 1/2/2/7.5/3.1

The reaction temperature was 500° C. and the contact time was 4.4 seconds. The molar ratio of $O_2$ to $C_3$ (propane) was 2. The propane conversion was 65.2 percent and the yields and selectivities were as shown in Table V:

TABLE V

|  | % Yield | % Selectivity |
|---|---|---|
| Acrylonitrile | 25.8 | 39.6 |
| HCN | 4.3 | 6.6 |

The catalyst for thi example was prepared as follows:

A catalyst having the composition 50% $VSb_5WO_x$+50% $Al_2O_3$ was prepared as follows. In a flask equipped for heating under a reflux there was placed 150 ml water and 5.4 $NH_4VO_3$. The mixture was stirred and heated until a clear solution was obtained, then 33.6 g $Sb_2O_3$ was added. The resulting slurry was stirred and boiled under reflux for 12-16 hours to effect the redox reaction between vanadium and antimony, in a manner similar to that shown in Example 1. It was then transferred to an open beaker an heated with sitrring. A solution of 12.45 g ammonium metatungstate in 25-30 ml water was added, and the heating and stirring continued to remove the bulk of the water. The resulting wet product was dried in air overnight at 110°-120° C. It was then ground to a fine powder and thoroughly mixed with 58.8 g hydrated alumina (85% $Al_2O_3$, tradename Catapal SB). This mixture was stirred with 64-65 ml water in which 7.5 ml acetic acid had been dissolved and then kneaded thoroughly until a semisolid mass having the consistency of wet dough was obtained. This product was dried at 100°–120° C. then further heated at 350° C. for 5 hours, screened to a desired particle size, and calcined in air at 610° C. for 3 hours.

EXAMPLES 43–45

The same catalyst was used in these examples as in Examples 13 and 14, but in the fixed bed ammoxidation of isobutane. Conditions and results are shown in Table VI.

TABLE VI

| | | Ammoxidation of Isobutane | | | | | | |
|---|---|---|---|---|---|---|---|---|
| Example No. | Catalyst[1] | Isobutane % Conv. | % Yield | | | % Selectivity | | |
| | | | MAN | AN | HCN | MAN | AN | HCN |
| 43 | $VSb_5WO_x$ | 40.5 | 6.4 | 3.2 | 2.9 | 15.9 | 3.2 | 7.2 |
| 44 | $VSb_5WO_x$ | 41.3 | 8.8 | 3.2 | 2.4 | 21.2 | 7.7 | 5.8 |
| | $C_4/NH_3/O_2/H_2O = 1/2/3/11.3/1.5$ | | | | | | | |
| | Contact time: 3.7 sec. | | | | | | | |
| 45 | $VSb_5WO_x$ | 39.3 | 4.0 | 2.6 | 2.5 | 10.1 | 6.5 | 6.5 |

MAN is methacrylonitrile
AN is acrylonitrile
Temp.: 500° C.
Contact time: 4.5 sec
Feed ratio: $C_4/NH_3/O_2/N_2/H_2O = 1/2/2/7.5/3$
catalyst support: 50% silica-alumina (20% $SiO_2$, 80% $Al_2O_3$)
calcination: @ 530° C. in air

EXAMPLE 46

A catalyst having the composition 50 wt % $VSb_5WO_x + 50$ wt % $Al_2O_3$ was prepared as follows: An aluminum gel was prepared by adding 58.8 g hydrated alumina, 85 wt % $Al_2O_3$, to a mixture of 206 ml distilled water and 29 g of acetic acid. A stable dispersion was obtained which after 3 to 4 hours stirring formed a soft non-flowing gel.

In a separate step 5.40 g of ammonium vanadate, dissolved in 150 ml of distilled water, was refluxed along with 33.6 g of $Sb_2O_3$ for about 16 hours. Following reflux 12.45 g of ammonium metatungstate was added to the hot slurry and the mixture was allowed to partly evaporate with constant stirring. It was then thoroughly mixed with the alumina gel. The resulting mixture was dried in an evaporating dish for about 16 hours at about 120° C.

The dried material was heat treated in air at 350° C. for 5 hours and then ground and screened and the 20 to 35 mesh particle size was collected. The screened material was finally heat treated at 610° C. in air for 3 hours.

EXAMPLE 47

A catalyst having the empirical formula 50 wt % $VSb_{3.5}P_{0.5}WO_x + 50$ wt % $Al_2O_3$ support was made as follows:

In a stirred flask equipped for heating under reflux, 3.81 g $NH_4VO_3$ were dissolved in 90 ml hot water. To the hot solution 16.6 g $Sb_2O_3$ were added, and the slurry was boiled under reflux for 16–18 hours overnight. There was ammonia evolution, and the vanadium antimonate mixture turned gray-green.

In a separate operation, 35.3 g hydrated alumina, 85 wt % $Al_2O_3$ were mixed with 127.2 ml $H_2O$ (cold) +14.1 g acetic acid (10 percent solution) and stirred until the suspension gelled. It took about 3 hours, and the gel was soft, homogeneous, with the consistency of thick cream.

Meanwhile, the vanadium antimonate slurry was transferred to a beaker. A solution of 8.80 g ammonium meta-tungstate in about 20 ml $H_2O$ and a solution of 2.15 g $(NH_4)_2HPO_4$ in $H_2O$ were then added, followed by the addition, with stirring (magnet) of the alumina gel. After partial evaporation, the mixture became too thick for stirring. It was then transferred to an evaporating dish, and the evaporation, following by drying overnight, was continued in an oven at 110°–120° C. The dried material was precalcined at 350° C. for 5 hours, screened to 20/35 mesh, then calcined 3 hours at 610° C.

EXAMPLE 48

A catalyst having the composition 50 wt % $VSb_5PWO_x + 50$ wt % $Al_2O_3$ was prepared as follows: 15.0 g of ammonium vanadate was dissolved in about 300 ml of hot distilled water. To this stirred solution was added 10.6 g of 99% $H_3PO_4$ in 25 ml of distilled water. The mixture was refluxed for about 16 hours then evaporated under nitrogen at 85°–90° C. for several hours and then dried at about 135° C. 5.36 g of this dried material was mixed along with 21.90 g of $Sb_2O_3$ and 8.10 g of ammonium metatungstate in 20 ml of distilled water. The resulting slurry was evaporated in an oven at about 120°–125° C. with frequent stirring and then dried in an oven for 6 hours. The dried material was mixed with 40.30 g of hydrated alumina, 85 wt % $Al_2O_3$ and compounded to a paste with 42 ml of distilled water and 5 ml of acetic acid. The mixture was dried at 120° C. in air.

The dried material was heat treated in air at 350° C. or 5 hours and then ground and screened and the 20 to 35 mesh particle size was collected. The screened material was finally heat treated at 610° C. in air for 3 hours.

EXAMPLE 49

A catalyst having the composition 50 wt % $VSb_{3.5}WO_x + 50$ wt % $Al_2O_3$ was prepared as follows: An alumina gel was prepared by adding 34.71 g hydrated alumina, 85 wt % $Al_2O_3$ to 125 cc of water, followed by the addition of 13.9 g of glacial acetic acid with stirring; after about 4 hours a gel formed.

In a separate operation 4.14 g of $NH_4VO_3$ was dissolved in 150 cc of hot water with stirring. 18.07 g of $Sb_2O_3$ was added and the mixture was refluxed with stirring overnight. 9.66 g of ammonium metatungstate dissolved in 40 cc of water was added to the refluxing mixture. This mixture was stirring for 15 minutes, placed in a 600 cc beaker, and the alumina gel was added while stirring. The mixture was concentrated by heating at 120° C. in an evaporating dish. It was then heat treated for 5 hours at 350° C. and then ground and screened. The 20 to 35 mesh particle size material was collected and calcined in air at 610° C. for 3 hours.

EXAMPLE 50

A catalyst having the composition 50 wt % $VSb_5WP_{0.5}O_x + 50$ wt % $Al_2O_3$ was prepared as follows: 19.54 g of $Sb_2O_3$ was added to a heated solution of 3.14 g of ammonuim vanadate in 90 ml of distilled water and the mixture was refluxed for about 16 hours. The mixture was then transferred to a beaker and heated with stirring. Aqueous solutions of 7.24 g of ammonium metatungstate and 1.77 g of ammoniumhydrogen phosphate were then added and the mixture was allowed to partly evaporate with constant stirring. To this was added a dispersion of hydrated alumina, 85 wt % $Al_2O_3$ prepared by mixing 35.3 g of hydrated alumina, 85 wt % $Al_2 O_3$ with 1.5 g acetic acid in 140 g of distilled water. The resulting mixture was first evaporated in a beaker with constant stirring then in an evaporating dish for about 16 hours at about 120° C.

The dried material was heat treated in air at 350° C. for 5 hours and then ground and screened and the 20 to 35 mesh particle size was collected. The screened material was finally heat treated at 610° C. in air for 3 hours.

In the ammoxidation runs of the following examples, the catalyst is in a tubular ⅜ inch I.D. stainless steel fixed bed reactor. The reactor is equipped with a preheat leg immersed in a temperature controlled molten salt bath. The feed is fed over the catalyst for the number of hours noted before the runs are started; the runs of each example last 30 minutes. In all runs the weight of propane per unit weight of catalyst per hour (WWH) was 0.150.

EXAMPLE 51

The gaseous feed components were metered through mass flow controllers into the bottom of the reactor tube through the preheat leg. The catalyst was a catalyst of Example 46. Water was introduced through a septum at the top of the preheat leg using a syringe pump. The reaction temperature was 500° C., and the molar feed ratios were 1 propane/2 $NH_3/3O_2/6.7N_2/3$-$H_2O$. The collection of data began after 25 hours. Analysis of the reactor effluent showed that yield and selectivity of propane to acrylonitrile were 29.3 and 36.0 percent respectively; yield and selectivity to propylene were 4.4 and 5.5 percent, respectively.

EXAMPLE 52

The gaseous feed components were metered through mass flow controllers into the bottom of the reactor tube through the preheat leg. The catalyst was a catalyst of Example 48. Water was introduced through a septum at the top of the preheat leg using a syringe pump. The reaction temperature was 500° C., and the molar feed ratios were 1 propane/2 $NH_3/3$ $O_2/6.7$ $N_2/3$ $H_2O$. The collection of data began after 25 hours. Analysis of the reactor effluent showed that propane selectivity to acrylonitrile was 34.0 percent; and selectivity to propylene was 21.3 percent. The combined selectivity to acrylonitrile plus propylene was much greater than without P in the catalyst as in Example 51.

EXAMPLE 53

The gaseous feed components were metered through mass flow controllers into the bottom of the reactor tube through the preheat leg. The catalyst was a catalyst of Example 50. Water was introduced through a septum at the top of the preheat leg using a syringe pump. The reaction temperature was 500° C., and the molar feed ratios were 1 propane/2 $NH_3/3$ $O_2/6.7$ $N_2/3$ $H_2O$. The collection of data began after 23 hours. Analysis of the reactor effluent showed that propane conversion was 72.3 percent, selectivity of propane to acrylonitrile was 38.4 percent and selectivity to propylene was 9.4 percent. The combined selectivity to desired products, acrylonitrile and propylene was 47.8 percent, compared to 41.5 percent in Example 51.

EXAMPLE 54

The gaseous feed components were metered through mass flow controllers into the bottom of the reactor tube through the preheat leg. The catalyst was the catalyst of Example 49. Water was introduced through a septum at the top of the preheat leg using a syringe pump. The reaction temperature was 500° C., and the molar feed ratios were 1 propane/2 $NH_3/3$ $O_2/6.7$ $N_2/3$ $H_2O$. The collection of data began after 24 hours. Analysis of the reactor effluent showed that propane conversion was 78.2 percent; yield and selectivity of propane to acrylonitrile were 27.9 and 35.6 percent, respectively; yield and selectivity to propylene were 4.5 and 5.8 percent, respectively.

EXAMPLE 55

The gaseous feed components were metered through mass flow controllers into the bottom of the reactor tube through the preheat leg. The catalyst was a catalyst of Example 47. Water was introduced through a septum at the top of the preheat leg using a syringe pump. The reaction temperature was 500° C., and the molar feed ratios were 1 propane /2 $NH_3/3$ $O_2/6.7$ $N_2/3$ $H_2O$. The collection of data began after 30 hours. Analysis of the reactor effluent showed that propane conversion was 86.2 percent; yield and selectivity of propane to acrylonitrile were 33.9 and 39.3 percent respectively; yield and selectivity to propylene were 4.2 and 5.9 percent, respectively. These results compared very favorably with Example 54, using the same catalyst except that it contained no P.

EXAMPLE 56

The gaseous feed components were metered through mass flow controllers into the bottom of the reactor tube through the preheat leg. The catalyst was a catalyst having the empirical composition $VSb_{3.5}P_{0.25}WO_x$, the same as Example 49 except for the P content. Water was introduced through a septum at the top of the preheat leg using a syringe pump. The reaction temperature was 500° C., and the molar feed ratios were 1 propane/2 $NH_3/3$ $O_2/6.7$ $N_2/3$ $H_2O$. The collection of data began after 23 hours. Analysis of the reactor effluent showed that propane conversion was 87.3 percent; yield and selectivity of propane to acrylonitrile were 32.7 and 37.5 percent respectively; yield and selectivity to propylene were 3.4 and 3.9 percent, respectively.

In the ammoxidation runs of the following examples, the catalyst is in a tubular ⅜ in I.D. stainless steel fixed bed reactor. The reactor is equipped with a preheat leg immersed in a temperature controlling salt bath. These runs differed from previous runs in that an excess of propane was employed, so that conversions were necessarily low, but selectivities to useful products were high.

EXAMPLE 57

A catalyst having the composition 50 wt % $VSb_4PWO_x + 50$ wt % $Al_2O_3$ was made as follows: 2.99 g of ammonium vanadate and 6.98 g of ammonium metatungstate (85 wt % WO$_3$ equivalent) was dissolved in 100 ml of distilled water along with 2.95 g of 85% H$_3$PO$_4$ in 20 ml of distilled water. The mixture was heated to boiling. 14.92 g of Sb$_2$O$_3$ was then added along with a mixture consisting of 29.41 g of hydrated alumina, 85 wt % Al$_2$O$_3$ dispersed in about 104 ml of a 4% acetic acid solution. The mixture was heated to near boiling until it thickened. The thickened mixture was then placed on an evaporating dish and dried in an oven at 110° C. for about 16 hours. The dried material was heated in air at 350° C. for five hours and then ground and screened and the 20 to 35 mesh particle size was collected. The screened material was then heat treated in air at 610° C. for 3 hours.

0.28 g of the material was examined as a catalyst for propane ammoxidation in a fixed bed microreactor using a gaseous feed mixture consisting of 5C$_3$H$_8$/1NH$_3$/2O$_2$/1H$_2$O, a contact time of about 0.3 seconds, and a reaction temperature of 470° C. Analysis of the product mixture showed 13.4% propane had converted with selectivities to the useful products, acrylonitrile and propylene, of 16.1 and 60.7%, respectively.

EXAMPLE 58

A catalyst having the composition 50 wt % VSb$_3$PWO$_x$+50 wt % Al$_2$O$_3$ was made as follows: 3.56 g of ammonium vanadate and 8.21 g of ammonium metatungstate (85 wt % WO$_3$ equivalent) were dissolved in 100 ml of distilled water along with 3.47 g of 85% H$_3$PO$_4$. 13.15 g of Sb$_2$O$_3$ was then added to the mixture and the resulting slurry was heated for about one hour at about 90° C. A mixture consisting of 29.41 g of hydrated alumina, 85 wt % Al$_2$O$_3$ dispersed in 4.2 g of acetic acid in 100 ml of distilled water was then added to the slurry. After addition of the alumina, the mixture began to thicken. The thickened mixture was diluted with about 100 ml of water and the mixture was evaporated to near dryness on a hot plate with constant stirring. The material was then dried in an oven at 100° C. for about 16 hours. The dried material was heated in air at 350° C. for five hours and then ground and screened and the 20 to 35 mesh particle size was collected. The screened material was then heat treated in air at 610° C. for 3 hours.

The material was examined as a catalyst for propane ammoxidation using the same reaction conditions as Example 57. Propane conversion was 19.5% and selectivities to acrylonitrile and propylene were 20.9 and 53.0%, respectively.

EXAMPLE 59

A catalyst having the composition 50 wt % VSbPWO$_x$+50 wt % Al$_2$O$_3$ was made as follows: 5.48 g of ammonium vanadate and 12.64 g of ammonium metatungstate (85 wt % WO$_3$ equivalent) were dissolved in 100 ml of distilled water along with 5.34 g of 85% H$_3$PO$_4$. 6.75 g of Sb$_2$O$_3$ was then added to the mixture and the resulting slurry was heated for about one hour at about 90° C. A mixture consisting of 29.41 g of hydrated alumina, 85 wt % Al$_2$O$_3$ dispersed in 4.2 g of acetic acid in 100 ml of distilled water

EXAMPLE 58

A catalyst having the composition 50 wt % VSb$_3$PWO$_x$+50 wt % Al$_2$O$_3$ was made as follows: 3.56 g of ammonium vanadate and 8.21 g of ammonium metatungstate (85 wt % WO$_3$ equivalent) were dissolved in 100 ml of distilled water along with 3.4 g of 85% H$_3$PO$_4$. 13.15 g of Sb$_2$O$_3$ was then added to the mixture and the resulting slurry was heated for about one hour at about 90° C. A mixture consisting of 29.41 g of hydrated alumina, 85 wt % Al$_2$O$_3$ dispersed in 4.2 g of acetic acid in 100 mil of distilled water was then added to the slurry. After addition of the alumina, the mixture began to thicken. The thickened mixture was diluted with about 100 ml of water and the mixture was evaporated to near dryness on a hot plate with constant stirring. The material was then dried in an oven at 100° C. for about 16 hours. The dried material was heated in air at 350° C. for five hours and then ground and screened and the 20 to 35 mesh particle size was collected. The screened material was then heat treated in air at 610° C. for 3 hours.

The material was examined as a catalyst for propane ammoxidation using the same reaction conditions as Example 57. Propane conversion was 19.5% and selectivities to acrylonitrile and propylene were 20.9 and 53.0%, respectively.

EXAMPLE 59

A catalyst having the composition 50 wt % VSbPWO$_x$+50 wt % Al$_2$O$_3$ was made as follows: 5.48 g of ammonium vanadate and 12.64 g of ammonium metatungstate (85 wt % WO$_3$ equivalent) were dissolved in 100 ml of distilled water along with 5.34 g of 85% H$_3$PO$_4$. 6.75 g of Sb$_2$O$_3$ was then added to the mixture and the resulting slurry was heated for about one hour at about 90° C. A mixture consisting of 29.41 g of hydrated alumina, 85 wt % Al$_2$O$_3$ dispersed in 4.2 g of acetic acid in 100 ml of distilled water was then added to the slurry. After addition of the alumina, the mixture began to thicken. The thickened mixture was diluted with about 100 ml of water and the mixture was evaporated to near dryness on a hot plate with constant stirring. The material was then dried in an oven at 100° C. for about 16 hours. The dried material was heated in air at 350° C. for five hours and then ground and screened and the 20 to 35 mesh particle size was collected. The screened material was then heat treated in air at 610° C. for 3 hours.

The material was examined as a catalyst for propane ammoxidation using the same reaction conditions as Example 57. Propane conversion was 20.7% and selectivities to acrylonitrile and propylene were 21.7 and 48.0%, respectively.

EXAMPLE 60

A catalyst having the composition 50 wt % VSb$_{3.5}$P$_{0.5}$W$_{0.5}$O$_x$+50 wt % Al$_2$O$_3$ was made as follows: 3.89 g of ammonium vanadate and 4.53 g of ammonium metatungstate (85 wt % WO$_3$ equivalent) were dissolved in 100 ml of distilled water along with 1.92 g of 85% H$_3$PO$_4$. 16.95 g of Sb$_2$O$_3$ was then added to the mixture and the resulting slurry was heated for about one hour at about 90° C. A mixture consisting of 29.41 g of hydrated alumina, 85 wt % Al$_2$O$_3$ dispersed in 4.2 g of acetic acid in 100 ml of distilled water was then added to the slurry. After addition of the alumina, the mixture began to thicken. The thickened mixture was diluted with about 100 ml of water and the mixture was evaporated to near dryness on a hot plate with constant stirring. The material was then dried in an oven at 100° C. for about 16 hours. The dried material was heated in air at 350° C. for five hours and then ground and screened and the 20 to 35 mesh particle size was collected. The screened material was then heat treated in air at 610° C. for 3 hours.

The material was examined as a catalyst for propane ammoxidation using the same reaction conditions as Example 57. Propane conversion was 19.6% and selectivities to acrylonitrile and propylene were 15.9 and 51.1%, respectively.

EXAMPLE 61

A catalyst having the composition 50 wt % $VSb_5P_{0.5}W_{0.5}O_x + 50$ wt % $Al_2O_3$ was made as follows: 3.01 g of ammonium vanadate and 3.51 g of ammonium metatungstate (85 wt % $WO_3$ equivalent) were dissolved in 100 ml of distilled water along with 1.48 g of 85% $H_3PO_4$. 18.76 g of $Sb_2O_3$ was then added to the mixture and the resulting slurry was heated for about one hour at about 90° C. A mixture consisting of 29.41 g of hydrated alumina, 85 wt % $Al_2O_3$ dispersed in 4.2 g of acetic acid in 100 ml of distilled water was then added to the slurry. After addition of the alumina, the mixture began to thicken. the thickened mixture was diluted with about 100 ml of water and the mixture was evaporated to near dryness on a hot plate with constant stirring. The material was then dried in an oven at 100° C. for about 16 hours. The dried material was heated in air at 350° C. for five hours and then ground and screened and the 20 to 35 mesh particle size was collected. The screened material was then heat treated in air at 610° C. for 3 hours.

The material was examined as a catalyst for propane ammoxidation using the same reaction conditions as Example 57. Propane conversion was 13.3% and selecitivites to acrylonitrile and propylene were 15.7 and 58.9%, respectively.

EXAMPLE 62

A catalyst having the composition 50 wt % $VSb_{3.5}P_{0.5}O_x + 50$ wt % $Al_2O_3$ was made as follows: 4.59 g of ammonium vanadate were dissolved in 100 ml of distilled water along with 2.26 g of 85% $H_3PO_4$. 20.04 g of $Sb_2O_3$ was then added to the mixture and the resulting slurry was heated for about one hour at about 90° C. A mixture consisting of 29.41 g of hydrated alumina, 85 wt % $Al_2O_3$ dispersed in 4.2 g of acetic acid in 100 ml of distilled water was then added to the slurry. After addition of the Catapal, the mixture began to thicken. The thickened mixture was diluted with about 100 ml of water and the mixture was evaporated to near dryness on a hot plate with constant stirring. The material was then dried in an oven at 100° C. for about 16 hours. The dried material was heated in air at 350° C. for five hours and then ground and screened and the 20 to 35 mesh particle size was collected. The screened material was then heat treated in air at 610° C. for 3 hours.

The material was examined as a catalyst for propane ammoxidation using the same reaction conditions as Example 57. Propane conversion was 15.9% and selectivities to acrylonitrile and propylene were 8.3 and 42.2%, respectively.

EXAMPLE 63

A catalyst having the composition 50 wt % $VSb_{3.5}P_{0.5}WO_x + 50$ wt % $Al_2O_3$ was made as follows: 3.37 g of ammonium vanadate and 7.85 g of ammonium metatungstate (85 wt % $WO_3$ equivalent) were dissolved in 100 ml of distilled water along with 1.66 g of 85% $H_3PO_4$. 14.69 g of $Sb_2O_3$ was then added to the mixture and the resulting slurry was heated for about one hour at about 90° C. A mixture consisting of 125 g of alumina sol (20 wt % $Al_2O_3$) was then added to the slurry. After addition of the sol, the mixture began to thicken. The thickened mixture was diluted with about 100 ml of water and the mixture was evaporated to near dryness on a hot plate with constant stirring. The material was then dried in an oven at 100° C. for about 16 hours. The dried material was heated in air at 350° C. for five hours and then ground and screened and the 20 to 35 mesh particle size was collected. The screened material was then heat treated in air at 610° C. for 3 hours.

The material was examined as a catalyst for propane ammoxidation using the same reaction conditions as Example 57. Propane conversion was 17.4% and selectivities to acrylonitrile and propylene were 18.5 and 53.5%, respectively.

EXAMPLE 64

A catalyst having the composition 50 wt % $VSb_{3.5}P_{0.5}WO_x + 50$ wt % $Al_2O_3$ was made as follows: 3.40 g of ammonium vanadate and 7.85 g of ammonium metatungstate (85 wt % $WO_3$ equivalent) were dissolved in 100 ml of distilled water along with 1.66 g of 85% $H_3PO_4$. 14.69 g of $Sb_2O_3$ was then added to the mixture along with about 5 g of concentrated nitric acid solution. The resulting slurry was heated for about one hour at about 90° C. A mixture consisting of 29.41 g of hydrated alumina, 85 wt % $Al_2O_3$ dispersed in 4.2 g of acetic acid in 100 ml of distilled water was then added to the slurry. After addition of the alumina, the mixture began to thicken. The thickened mixture was diluted with about 100 ml of water and the mixture was evaporated to near dryness on a hot plate with constant stirring. The material was heated in air at 350° C. for five hours and then ground and screened and the 20 to 35 mesh particle size was collected. The screened material was then heat treated in air at 610° C. for 3 hours.

The material was examined as a catalyst for propane ammoxidation using the same reaction conditions as Example 57. Propane conversion was 19.5% and selectivities to acrylonitrile and propylene were 20.2 and 50.1% respectively.

EXAMPLE 65

A catalyst having the composition 50 wt % $VSb_{3.5}P_{0.5}WO_x + 50$ wt % $Al_2O_3$ was made as follows: 3.20 g of ammonium vanadate and 7.38 g of ammonium metatungstate (85 wt % $WO_3$ equivalent) were dissolved in 100 ml of distilled water along with 1.56 g of 85% $H_3PO_4$. 127.59 g of antimony oxide sol was then added to the mixture along with 3.75 g of oxalic acid. The resulting slurry was heated for about one hour at about 90° C. A mixture consisting of 29.41 g of hydrated alumina, 85 wt % $Al_2O_3$ dispersed in 4.2 g of acetic acid in 100 ml of distilled water was then added to the slurry. After addition of the alumina, the mixture began to thicken. The thickened mixture was diluted with about 100 ml of water and the mixture was evaporated to near dryness on a hot plate with constant stirring. The material was then dried in an oven at 100° C. for about 16 hours. The dried material was heated in air at 350° C. for five hours and then ground and screened and the 20 to 35 mesh particle size was collected. The screened material was then heat treated in air at 610° C. for 3 hours.

The material was examined as a catalyst for propane ammoxidation using the same reaction conditions as Example 57. Propane conversion was 18.5% and selectivities to acrylonitrile and propylene were 15.8 and 48.6, respectively.

The following are additional catalyst compositions of the invention containing promoting amounts of phosphorus. When these are used under the conditions of Example 57 to ammoxidize propane, similarly high total selectivities to acrylonitrile plus propylene result.

50 wt % $VSb_5Sn_{0.5}Te_{0.5}Fe_{0.5}P_{0.5}WO_x$+50 wt % $Al_2O_3$
50 wt % $VSb_{3.5}P_{0.5}W_{0.5}Mo_{0.5}O_x$+50 wt % $Al_2O_3$
50 wt % $VSb_{3.5}P_{0.5}W_3O_x$+25 wt % $Al_2O_3$+25 wt % $SiO_2$
50 wt % $VSb_{10}CoNiP_{0.5}WO_x$+50 wt % $Al_2O_3$
50 wt % $VSb_5PWO_x$+40 wt % $Al_2O_3$+10 wt % MgO
50 wt % $VSb_3P_{0.5}WCs_{0.01}O_x$+50 wt % $Al_2O_3$
50 wt % $VSb_{10}P_3CrWO_x$+50 wt % $Al_2O_3$
50 wt % $VSbP_{0.5}B_3O_x$+40 wt % $Al_2O_3$+10 wt % $Nb_2O_5$

As will be evident to those skilled in the art, various modifications of this invention can be made or followed in the light of the foregoing disclosure and discussion without departing from the spirit and scope of the disclosure or from the scope of the claims.

We claim:

1. A process for the ammoxidation of a paraffin selected from propane and isobutane to make acrylonitrile and methacrylonitrile, respectively, by the catalytic vapor phase reaction of such a paraffin in admixture with oxygen and ammonia by contact with a complex metal oxide catalyst which is essentially free of bismuth, and has the elements and the proportions which are represented by the following empirical formula:

$VSb_mA_aD_bC_cO_x$, where
A is one or more of W, Sn, B Mo and Ge;
D is one or more of Fe, Co, Ni, Cr, Mn, Cu, Pb, Zn, Se, Te and As;
C is one or more of an alkali metal, Ca, Sr, Ba, Tl and where m is greater than 1 and up to 20; a is 0.2-10; b is 0-5; c is 0-1; a is equal to or less than m; b is equal to or less than m; wherein x is determined by oxidation state of the other elements present, and wherein the antimony has an average valency higher than +3 and the vanadium has an average valency lower than +5, wherein A includes at least 0.2 atoms of W, crystalline $Sb_2O_4$ is present in said catalyst, and wherein the foregoing catalyst is on an inorganic oxide support material selected from silica, alumina, titania, zirconia, silica-niobia, silica-zirconia, silica-titania, silica-alumina, $Nb_2O_5$ and magnesia.

2. A process of claim 1 wherein m is 2-10.
3. A process of claim 1 wherein m is 3-7.
4. A process of claim 1 wherein said support contains 20 to 100 weight percent alumina and is selected from silica-alumina and alumina.
5. A process of claim 1 wherein said support contains 50 to 100 weight percent alumina and is selected from alumina and silica-alumina.
6. A process of claim 4 wherein A includes at least 0.4 atoms of W per atom of V.

7. A process of claim 1 wherein said support is selected from silica-alumina and alumina having 20 to 100 weight percent alumina; silica-titania and titania having 20-100 weight percent titania; silica-zirconia and zirconia having 80-100 weight percent zirconia; and silica-niobia and niobia having 30-100 weight percent niobia ($Nb_2O_5$).

8. A process of claim 1 wherein b is at least 0.2.
9. A process of claim 6 wherein b is at least 0.2.
10. A process of claim 5 wherein A includes at least 1 atom of W per atom of V.
11. A process of claim 1 wherein said support contains 60 to 100 weight percent alumina and is selected from alumina and silica-alumina.
12. A process of claim 1 wherein A includes at least 0.4 atoms of W per atom of V.
13. A process of claim 2 wherein A includes at least 0.4 atoms of W per atom of V.
14. A process of claim 7 wherein A includes at least 0.4 atoms of W per atom of V.
15. A process of claim 11 wherein A includes at least 0.4 atoms of W per atoms of V.
16. A process according to any one of the preceding claims wherein said catalyst, in addition to the elements and proportions represented by said empirical formula, contains P as a part of said complex catalyst in an amount up to 10 atoms of P per atom of V.
17. A process of any one of claims 1 to 15 wherein said paraffin is propane.
18. A process for the amoxidation of a paraffin selected from propane and isobutane to make acrylonitrile and methacrylonitrile, respectively, by the catalytic vapor phase reaction of such a paraffin in admixture with oxygen and ammonia by contact with a complex metal oxide catalyst, which is essentially free of bismuth, having the elements and proportions which are represented by the following empirical formula:

$VSb_mA_aD_bC_cO_x$, where
A is one or more of W, Sn, B, Mo and Ge and includes at least 0.2 atoms of W per atom of V;
D is one or more of Fe, Co, Ni, Cr, Mn, Cu, Pb, Zn, Se, Te and As;
C is one or more of an alkali metal, Ca, Sr, Ba, Tl and where m is greater than 1 and up to 20; a is 0.4-10; b is 0-5; c is 0-1; a is equal to or less than m; b is equal to or less than m; wherein x is determined by the oxidation state of the other elements present, and wherein the antimony has an average valency higher than +3 and the vanadium has an average valency lower than +5, wherein crystalline $Sb_2O_4$ is present in said catalyst, and wherein the foregoing catalyst is on an inorganic oxide support material selected from alumina and silica-alumina which is 50 to 100 weight percent alumina.

19. A process of claim 18 wherein A includes at least 0.4 atoms of W per atom of V.
20. A process according to claim 18 wherein said catalyst, in addition to the elements and proportions represented by said empirical formula, contains P as a part of said complex catalyst in an amount up to 10 atoms of P per atom of V.
21. A process according to claim 18 wherein said catalyst, in addition to the elements and proportions represented by said empirical formula, contains P as a part of said complex catalyst in an amount of 0.1 to 5 atoms of P per atom of V.

22. A process according to claim 19 wherein said catalyst, in addition to the elements and proportions represented by said empirical formula, contains P as a part of said complex catalyst in an amount up to 10 atoms of P per atom of V.

23. A process according to claim 19 wherein said catalyst, in addition to the elements and proportions represented by said empirical formula, contains P as a part of said complex catalyst in amount of 0.1 to 5 atoms of P per atom of V.

* * * * *